United States Patent
Krivitski

(12)
(10) Patent No.: US 6,308,737 B1
(45) Date of Patent: Oct. 30, 2001

(54) METHOD AND APPARATUS FOR SELECTIVELY REVERSING FLOW BETWEEN A DIALYZER AND A PATIENT ACCESS

(75) Inventor: Nikolai M. Krivitski, Ithaca, NY (US)

(73) Assignee: Transonic Systems, Inc., Ithaca, NY (US)

( * ) Notice: Subject to any disclaimer, the term of this patent is extended or adjusted under 35 U.S.C. 154(b) by 0 days.

(21) Appl. No.: 09/524,452

(22) Filed: Mar. 10, 2000

(51) Int. Cl.$^7$ ...................................................... F16K 11/10
(52) U.S. Cl. ............................ 137/597; 251/331; 604/6.1
(58) Field of Search .............................. 137/597, 625.43, 137/625.48; 251/4, 61.1, 331; 604/6.1

(56) References Cited

U.S. PATENT DOCUMENTS

| | | | |
|---|---|---|---|
| 3,585,995 | * | 6/1971 | Perkins et al. ........................... 604/4 |
| 3,744,524 | * | 7/1973 | Blau ....................................... 137/636 |
| 4,037,622 | * | 7/1977 | Osheroff et al. ...................... 137/597 |
| 4,324,662 | | 4/1982 | Schnell . |
| 4,586,920 | | 5/1986 | Peabody . |
| 4,821,996 | | 4/1989 | Bellotti et al. . |
| 4,885,087 | | 12/1989 | Kopf . |
| 4,898,669 | | 2/1990 | Tesio . |
| 4,946,434 | | 8/1990 | Plaisted et al. . |
| 5,605,630 | | 2/1997 | Shibata . |
| 5,650,071 | | 7/1997 | Brigger et al. . |
| 5,771,914 | * | 6/1998 | Ling et al. ............................... 137/1 |
| 5,894,011 | | 4/1999 | Prosl et al. . |

* cited by examiner

Primary Examiner—John Fox
(74) Attorney, Agent, or Firm—Brian B. Shaw Esq.; Stephen B. Salai, Esq.; Harter, Secrest & Emery LLP

(57) ABSTRACT

A diverter for selectively providing fluid communication between ports to a common chamber is disclosed. The diverter includes a resilient deformable common chamber having a plurality of ports. Upon deforming the common chamber along a given line, fluid communication between selected ports is precluded, which flow preclusion is used to effectively reverse a flow direction in a circuit connected to the diverter.

10 Claims, 10 Drawing Sheets

METHOD AND APPARATUS FOR SELECTIVELY REVERSING FLOW BETWEEN A DIALYZER AND A PATIENT ACCESS

FIELD OF THE INVENTION

The present invention relates to a flow diverter for selectively changing a flow direction in a connected line, and particularly to systems for replacement of kidney function in patients with end stage renal disease (ESRD), and more particularly to the treatment of ESRD by means of hemodialysis. In hemodialysis systems, the current invention provides an apparatus for selectively controlling the direction of flow in a portion of a blood circuit of a patient undergoing hemodialysis. Specifically, in the blood circuit comprising the closed loop through the patient's vascular system and through the hemodialysis machine, this invention relates to changing the direction of flow on the patient side, that is, to and from the patient's vascular system, without altering flow through the hemodialysis apparatus.

BACKGROUND OF THE INVENTION

In present day medical practice, hemodialysis is the standard therapy for treating ESRD. This therapy involves dialyzing the patient's blood several times a week. During treatment, the patient's vascular system is connected to a hemodialysis machine for sessions lasting several hours. This connection forms a blood circuit whereby blood is drawn from the patient through a needle connected to a patient access, cycled through a hemodialysis machine that removes waste products including water, urea, and other impurities from the blood, and returned to the patient access via a second blood line and needle.

The functional interface between the patient and the extracorporeal circuit is the patient or vascular access, from which blood is withdrawn and to which the externally treated blood is returned. To facilitate removal and return of blood, the patient access may have specialized connections allowing mating of separate arterial and venous blood lines, or the access may be cannulated with a hollow needle which is then connected to arterial and venous blood lines. Vascular access has been called the "Achilles' heel of dialysis" because of the frequent morbidity associated with maintenance and utilization of the access. A malfunctioning vascular access is not trivial, as the access represents a conduit for the passage of blood to the artificial kidney. Without treatment via the external kidney, toxin accumulation in the body is rapid and can be deadly.

One of the difficulties that can arise in chronic hemodialysis is maintaining adequate blood flow during treatment sessions. When flow rates decrease significantly during a session, the attendant could in many cases restore adequate flow by switching the blood lines. In current practice, the attendant must usually turn off the hemodialysis machine. This process lengthens the dialysis session while the machine is primed and restarted. In addition, switching the blood lines involves disconnecting the lines, which can cause bleeding and allow air to enter the lines. Disconnecting the lines also breaks the microbe barrier, increasing the possibility of infection.

Another difficulty that often arises with chronic hemodialysis is the possibility that the patient will develop a thrombus or blood clot that partially or wholly occludes a vascular access created by a fistula or vascular graft. When a fistula or graft becomes blocked, surgery is frequently needed to restore the venous access to a useful condition or replace the access site. A balloon angioplasty may be used to enlarge the lumen of the fistula or graft and prevent the immediate formation of thrombosis, thereby extending the life of the access. When a site can no longer be restored, it must be replaced. Replacing an access is a serious matter because patients have only a limited number of access sites for A/V fistulas and PTFE grafts.

Accordingly, an object of the present invention is to provide for the easy and convenient selection of which needle or catheter will be used to draw blood from the access and which will be used to return blood to the access at any particular time during hemodialysis treatment sessions, wherein such flow reversal can be employed in assessing access maintenance. Another object of this invention is to have a device that is compatible with high rates of flow in dialysis methods which utilize catheters. Yet another object of this invention is to accomplish the flow reversal function while minimizing the amount of turbulence associated with blood flow through the device. Still another object of the invention is to provide a device enhances safe use. A further object of the invention is to minimize stagnant flow regions in the device. Still another object of this invention is to provide a device that is easily added to existing hemodialysis set ups and treatment programs. Still another object of this invention is to provide a low cost, easily manufactured, sterile disposable device compatible with the rest of the blood circuit.

SUMMARY OF THE INVENTION

The present invention provides for the ready and reversible redirection of flow through a circulating system. The present invention finds particular application in the field of access management and particularly to those systems employing dilution technology.

Specifically, it has been found that measurements of vascular access recirculation and vascular access flow during dialysis are possible with "Ultrasound Dilution." Ultrasound Dilution uses changes that occur in the velocity of an ultrasound signal when blood is diluted with saline, instead of the traditional measurement of differences in temperature or dye concentration following an indicator infusion. Ultrasound travels through blood more quickly than it does through saline. Thus, when a bolus of saline is injected into the bloodstream, it dilutes the blood and reduces the velocity of the ultrasound signal. This reduction in the time it takes for the ultrasound signal to pass between sensors can be measured using ultrasound transit-time technology. By comparing the curves produced with the venous and arterial sensors after infusions of saline, it is possible to calculate recirculation, access flow and cardiac output. The disclosure of U.S. Pat. No. 5,685,989 naming Nikolai M. Krivitski and David R. MacGibbon as inventors, issuing Nov. 11, 1997 is hereby expressly incorporated by reference.

The determination of access flowing using this technology requires a reversal between the lines that draw blood and introduce blood to the access. That is, it is necessary to readily select which needle or catheter will be used to draw blood from the access and which will be used to return blood to the access at any particular time during hemodialysis treatment sessions. By allowing ready "reversal" of the blood flow, the present invention assists in access management including the determination of access flow, recirculation and cardiac output.

The present invention provides an apparatus for selectively diverting flow between ports of a common chamber so that flow through a needle or catheter in the patient access can effectively be reversed. In addition, the present invention may be manufactured at a sufficiently reduced cost to promote single use of the device, thereby reducing the risks associated with on-site sterilization techniques.

The present flow diverter includes a resilient deformable common chamber having a plurality of ports, wherein the chamber includes opposing interior surfaces that contact upon deformation of the chamber. Upon a sufficient deformation, the contacting surfaces form a fluid barrier within the chamber and thereby determine the permissible flow with respect to the ports. Preferably, the chamber is sufficiently deformable to contact opposing interior surfaces in a plurality of configurations to provide selective fluid communication between the ports.

In a preferred configuration, the flow diverter of the present invention can become an integral part of an extracorporeal circuit, allowing for blood passage to the artificial kidney (dialyzer) through the use of tubing similar to conventional arterial and venous blood lines.

The present invention further contemplates a method of reversing flow between the lines withdrawing blood and introducing processed blood to the patient access. The method includes fluidly connecting a common chamber to a source inlet, a source outlet, a device inlet and a device outlet; and selectively deforming the common chamber to contact opposing interior surfaces of the chamber to preclude fluid flow between the source inlet and the device inlet.

DETAILED DESCRIPTION OF THE PREFERRED EMBODIMENTS

Figure 1:
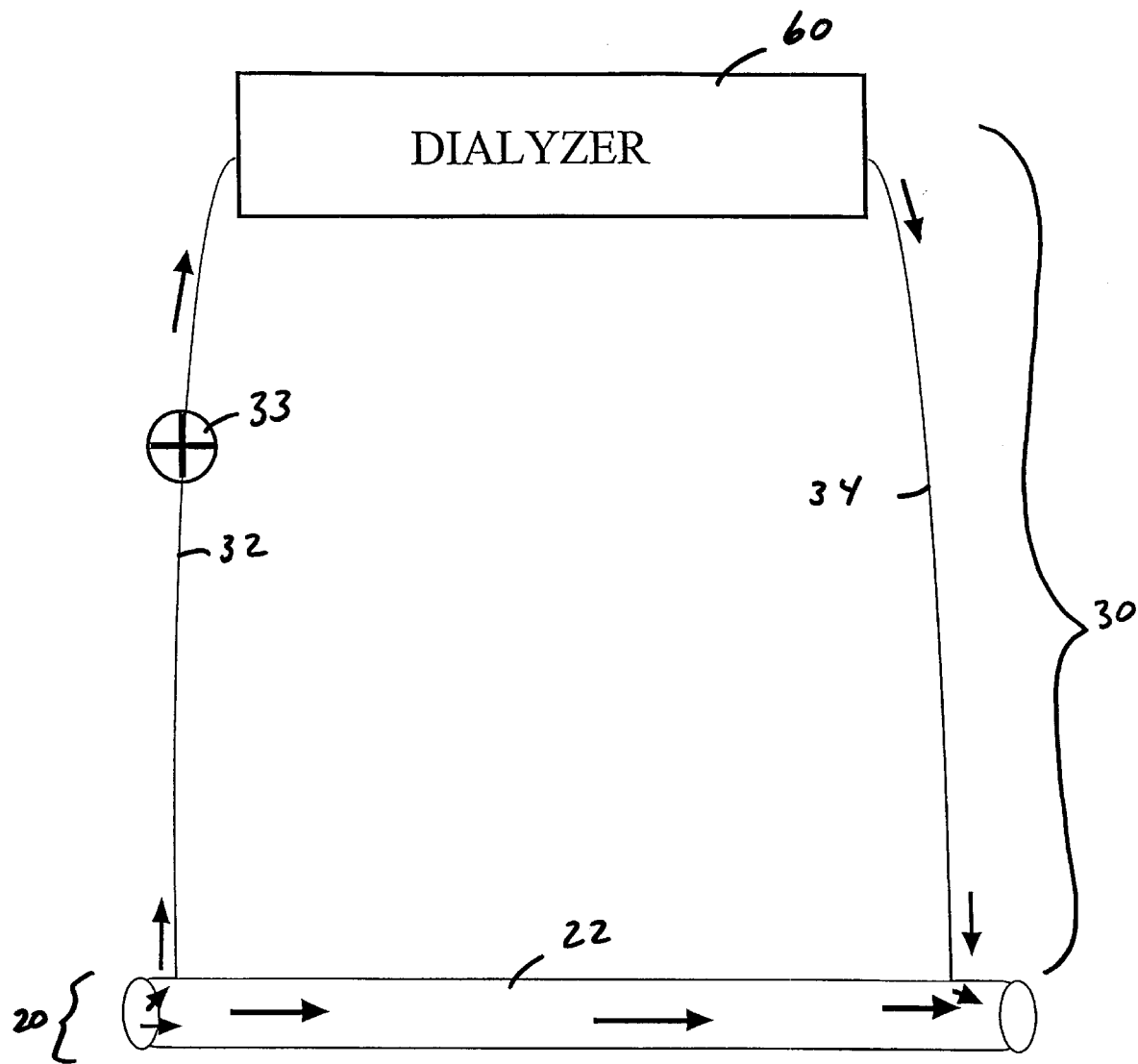
FIG. 1 is a schematic representation of a normal line configuration of a dialysis circuit.

Referring to FIG. 1, a hemodialysis circulating system is shown. Although the present invention is described in connection with a hemodialysis circulating system, it is understood the diverter may be employed in any fluid system.

The circulating system 10 includes a patient circuit 20 and an extracorporeal system 30. The patient circuit 20 includes the natural vascular flow paths in the body as well as a patient access 22. The extracorporeal circulation system 30 extends between the patient access 22 and a dialyzer 60 and includes interconnecting tubing or lines 50.

Patient Access

The patient access 22 may be any of a variety of shunts, grafts or fistulae. Traditionally, access to the patient's blood stream has been provided by an arterio/venous ("A/V") fistula or by a polytetrafluoroethylene ("PTFE") graft. An A/V fistula is a surgical construct joining an artery to a vein. The shunting of blood from an artery to a vein increases pressure on the vein, which pressure enlarges its diameter and thickens its walls. A fully developed fistula can be punctured with needles to access the patient's blood system. A PTFE graft is an artificial blood vessel used to connect the artery to the vein. The material used for the graft is suitable for puncturing with needles to achieve the necessary access to the patient's blood system. A third method of obtaining access for hemodialysis is to use percutaneous catheters which allow blood to be withdrawn from one lumen and returned by a second lumen.

Extracorporeal Circuit

The extracorporeal circuit 30 extends from the patient access 22 to the dialyzer 60 and back to the patient access. The typical extracorporeal circuit 30 includes an arterial line 32 conducting blood from the patient access to the dialyzer 60 and a venous line 34 conducting blood from the dialyzer to the patient access 22.

The extracorporeal circuit 30 may include a pump 33 for drawing blood from the patient access 22 to the dialyzer 60 and returning the processed blood to the patient. A roller pump is often employed as the external pump 33 which is often integrated into the dialysis machine 60. Alternatively, the pump 33 may be located in the arterial line 32. The pump 33 provides the negative pre-pump and positive post-pump pressure needed facilitate flow through the extracorporeal system 30. Although the present invention is described in terms of a roller pump, it is understood the extracorporeal circuit may be used with any of a variety of pumps.

The flow of the blood through the extracorporeal circuit 30 between the patient access 22 and the dialyzer 60 may be in either a normal or a reversed configuration. Referring to FIG. 1, the normal configuration is shown, wherein the arterial line 32 to the dialyzer 60 withdraws blood from an upstream location in the patient access 22. The blood then passes through the dialyzer 60 to return through the venous line 34 to be introduced into the patient access 22 at a location downstream from the withdrawal of the blood.

Figure 2:
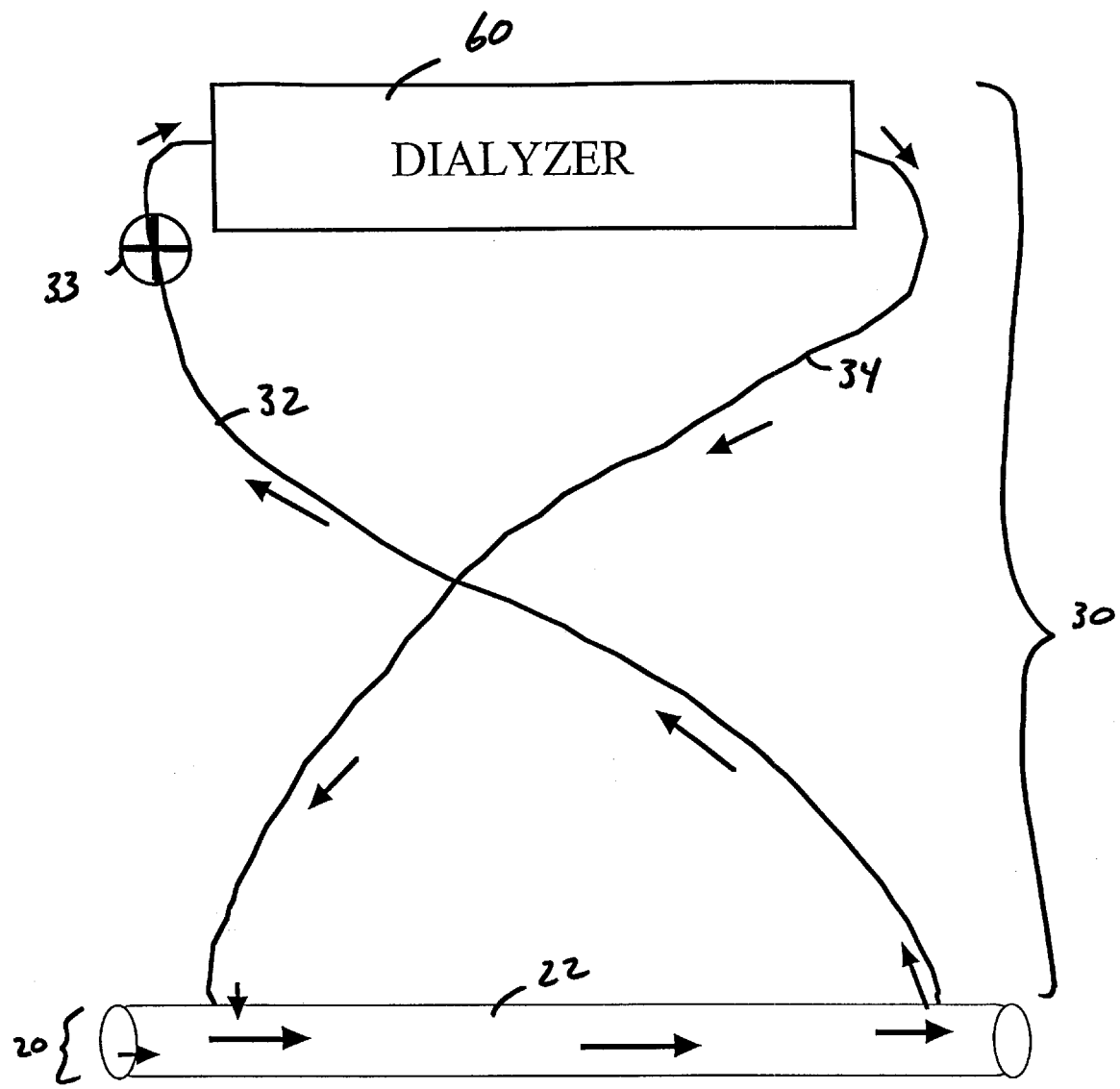
FIG. 2 is a schematic representation of a reversed line configuration of a dialysis circuit.
Figure 3:
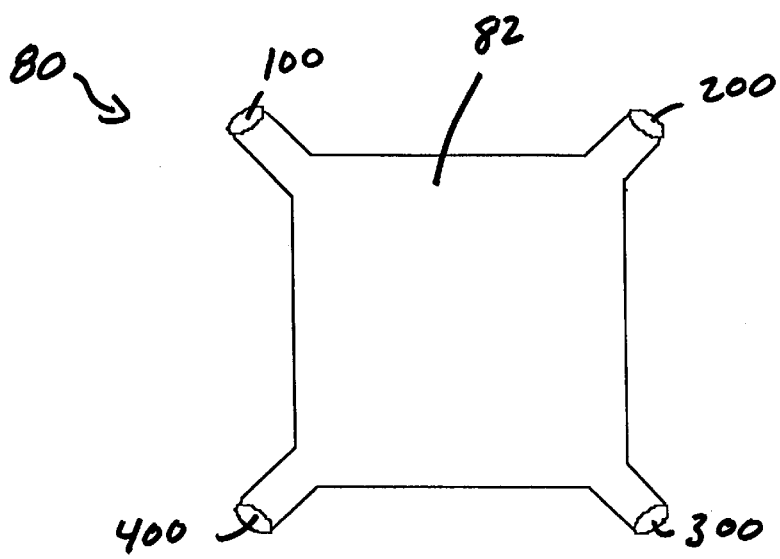
FIG. 3 is a top plan view of the flow diverter.

Referring to FIG. 2, the lines of the extracorporeal circuit 30 are shown in a reversed configuration. In the reversed configuration, the arterial line 32 to the dialyzer 60 withdraws blood from the patient access 22 at a downstream location. The withdrawn blood is passed through the dialyzer 60 and returned through the venous line 34 to an upstream location in the access 22. Thus, a portion of the blood that has passed through the dialyzer 60 and been introduced into the access 22 is subsequently withdrawn at the downstream location in the access.

As used herein, reversing the direction of flow in the blood circuit 30 means drawing blood through the needle which had previously been used to return blood to the patient and returning blood through the needle which had previously been used to draw blood from the patient without changing the direction that blood circulates through the hemodialysis machine. This change is also referred to herein as flow reversal or flow reversal in the patient portion of the blood circuit.

It has been found advantageous to selectively switch the blood flow in the extracorporeal circuit 30 between a normal line configuration and a reversed line configuration during a given session with a patient. The diverter 80 of the present invention may be fluidly connected to the extracorporeal circuit 30 and provide for selective flow paths through the circuit.

Referring to FIGS. 3–6, the diverter 80 includes a common chamber 82 having a plurality of ports 100, 200, 300 and 400. The common chamber 82 is a resilient and deformable member. The common chamber 82 includes an interior surface 83, wherein portions of the interior surface are selectively contacted by deformation of the chamber. These selectively contacting portions are referred to as opposing. The chamber 82 is sufficiently deformable such that upon contacting opposing portions of the interior surface 83 a barrier to fluid flow is created. The common chamber 82 is sufficiently resilient such that upon release of the deformation force, the interior surfaces 83 of the common chamber separate as the chamber resumes its relaxed state and the flow barrier is terminated. The common chamber 82 has deformation lines along which the chamber may be deformed to contact the interior surfaces 83 and form the interior barrier.

Figure 5:
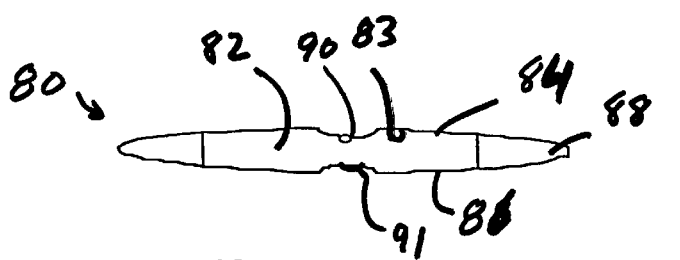
FIG. 5 is a cut away view showing interior surface features.
Figure 6:
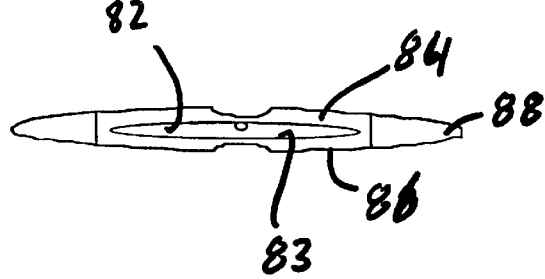
FIG. 6 is a cross sectional view taken along lines 6—6 of FIG. 4.

As shown in FIGS. 5 and 6, the common chamber 82 generally has a bottom wall 84 and a top wall 86 joined about a periphery 88. While a side wall may be employed intermediate the top wall 86 and the bottom wall 88 at the periphery, a preferred configuration is formed with the top wall and side wall joined at a common periphery. It is anticipated the top wall 86 and the bottom wall 88 are slightly curvilinear to define a generally pillow shaped cross sectional profile. The common chamber 82 is formed of a sufficiently resilient material that as opposing portions of the top wall 86 and the bottom wall 88 are urged together the walls slightly stretch to form a line of contact, which forms a fluid barrier. That is, the material of the common chamber 82 is sufficiently compliant that folds are not formed as the opposing surfaces are urged together.

Further, the common chamber 82 is selected such that upon applying a line of constriction, or bias, the opposing interior surfaces 83 contact along a line extending from one edge of the chamber to a spaced edge of the chamber, while still forming an open passage spaced from the contacting interior surfaces. That is, the contacting portions of the interior surfaces 83 form a continuous barrier that precludes fluid flow between two of the ports.

The interior surface 83 of the common chamber 82 may include features for assisting formation of the barrier upon contact of the opposing portions. For example, one of the top wall 86 and the bottom wall 88 may include a ridge 90 or ribs which contact the opposing wall upon deforming the chamber 82. It is also contemplated one wall may include a ridge and the remaining wall includes a groove or trough 91 sized to receive the ridge 90. While the present configuration is constructed such that common chamber 82 returns to the relaxed state upon removing the deformation force, it is contemplated the interior surfaces 83 could be configured to releasably engage and remain engaged after removal of the deformation force. That is, the interior surfaces 83 may function similar to a resealable container such as a ZIP LOCK™ bag. The engaged walls of the common chamber 82 could be released by flexing the chamber along a particular axis, thereby permitting fluid flow between the previously blocked ports.

As shown in FIG. 5, the diverter 80 may be constructed of a material to provide a top wall 86 and a bottom wall 88 having sufficient thinness that a profile of the interior surface 83 is complementary to a profile of an exterior surface. Conversely, as shown in FIG. 6, the top wall 86 and the bottom wall 88 may have a sufficient thickness that the interior and exterior profiles are not coincident.

Figure 4:
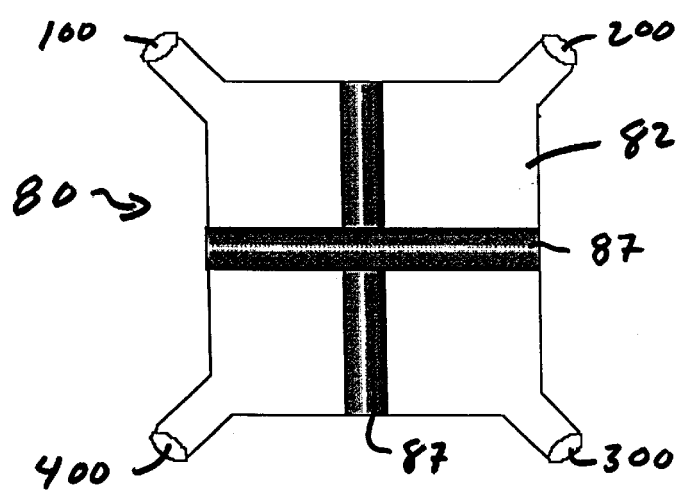
FIG. 4 is a top plan view of the flow diverter showing, clamping lines for different flow configurations.

Referring to FIGS. 4–6, the exterior of the common chamber 82 may also include features to assist in contacting the necessary interior surfaces. In one configuration, the exterior surface may include grooves or recesses 87 along the deformation lines. These exterior surface features 87 assist the operator in locating the clamping lines.

The particular interior surface features may be selected in cooperation with the number of ports and the anticipated flow diversions to be accomplished by the diverter 80. In a first configuration, the common chamber 82 has a generally rectangular and preferred square periphery. The diverter 82 includes four ports 100, 200, 300 and 400, wherein the ports are generally located at the corners of the rectangular profile. Each port is in fluid communication with the common chamber and hence with each remaining port. Although the ports 100, 200, 300 and 400 are shown as equi-spaced it is understood the ports may be asymmetrically spaced about the common chamber. In addition the ports 100, 200, 300 and 400 may be color coded to assist in set up and use of the extra corporeal circuit 30.

Figure 13:
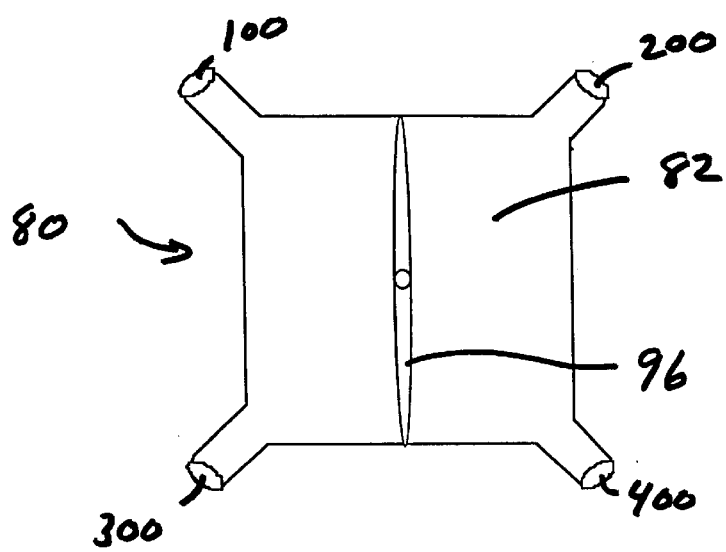
FIG. 13 is a schematic view showing a baffle for selectively permitting or precluding flow between adjacent ports.
Figure 14:
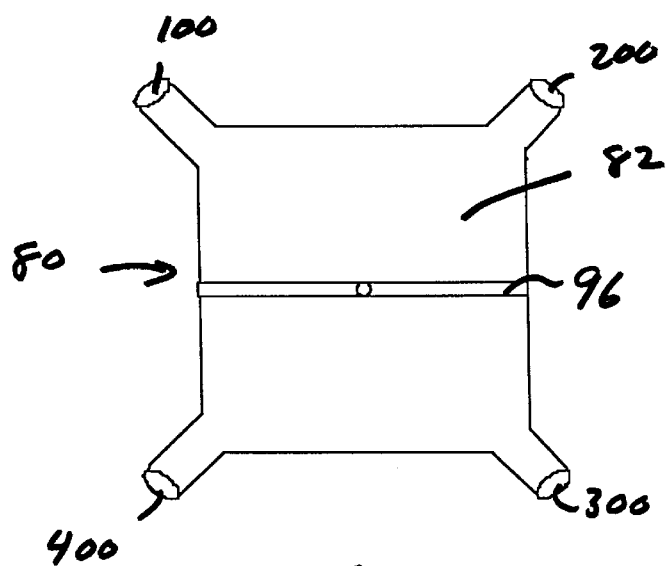
FIG. 14 is a schematic view showing an alternative baffle for selectively permitting or precluding flow between adjacent ports.
Figure 15:
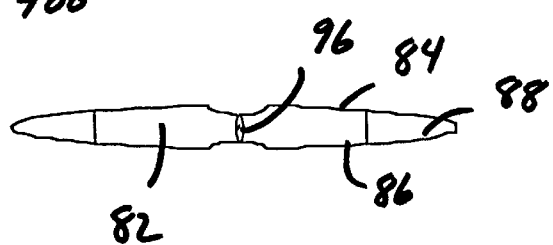
FIG. 15 is a schematic side elevational view showing the baffle in a first chamber configuration.
Figure 16:
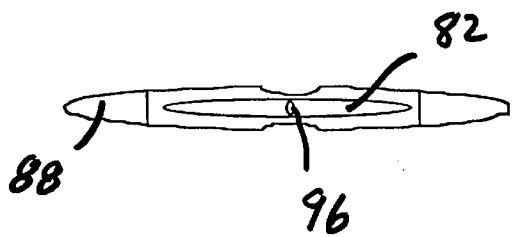
FIG. 16 is a schematic side elevational view showing the baffle in a second chamber configuration.

Referring to FIGS. 13–16, the chamber 82 may include a movable baffle 96. In this configuration, the common chamber 82 has a square periphery and the baffle 96 is rotatable about an axis passing through a center of the chamber 82. The baffle 96 has a length and height sufficient to substantially preclude fluid flow between the baffle and the adjacent top wall 86 and bottom wall 88. The baffle 96 may be operably located along line N—N, thus providing for fluid communication between ports 100 and 300, and between ports 200 and 400. The baffle 96 can then be rotated to lie along line R—R, thereby fluidly connecting ports 100 and 400, and 200 and 300 to provide for reversed flow. The baffle 96 and the chamber 82 may be configured to have the baffle slightly stress or deform the chamber as the baffle assumes the operable positions, as shown in FIGS. 13 and 14.

As shown in FIGS. 7–12, the diverter 80 is operably located in the extracorporeal circuit 30. Specifically, an upstream needle 14 is located in the patient access 22 and is connected to port 300 of the common chamber through an upstream (with respect to access flow direction) line 52. Port 100 of the common chamber 82 is connected to the input of the dialyzer 60 through a dialyzer arterial line 54. Typically, the dialyzer arterial line 54 includes the pump 33. Blood passes through the dialyzer 60 to exit via a dialyzer venous line 56 which connects to the common chamber 82 at port 200. The common chamber 82 is then connected by port 400 to a downstream (with respect to access flow direction) needle 16 in the patient access via a downstream line 58. Although needles are described as providing penetration of the patient access, it is understood that any of a variety of devices can be used and the invention is not limited to a particular type of access. Further, in this configuration, flow through the dialyzer arterial line 54 is always in the same direction and flow through the dialyzer venous line 56 also remains in a constant direction.

Figure 7:
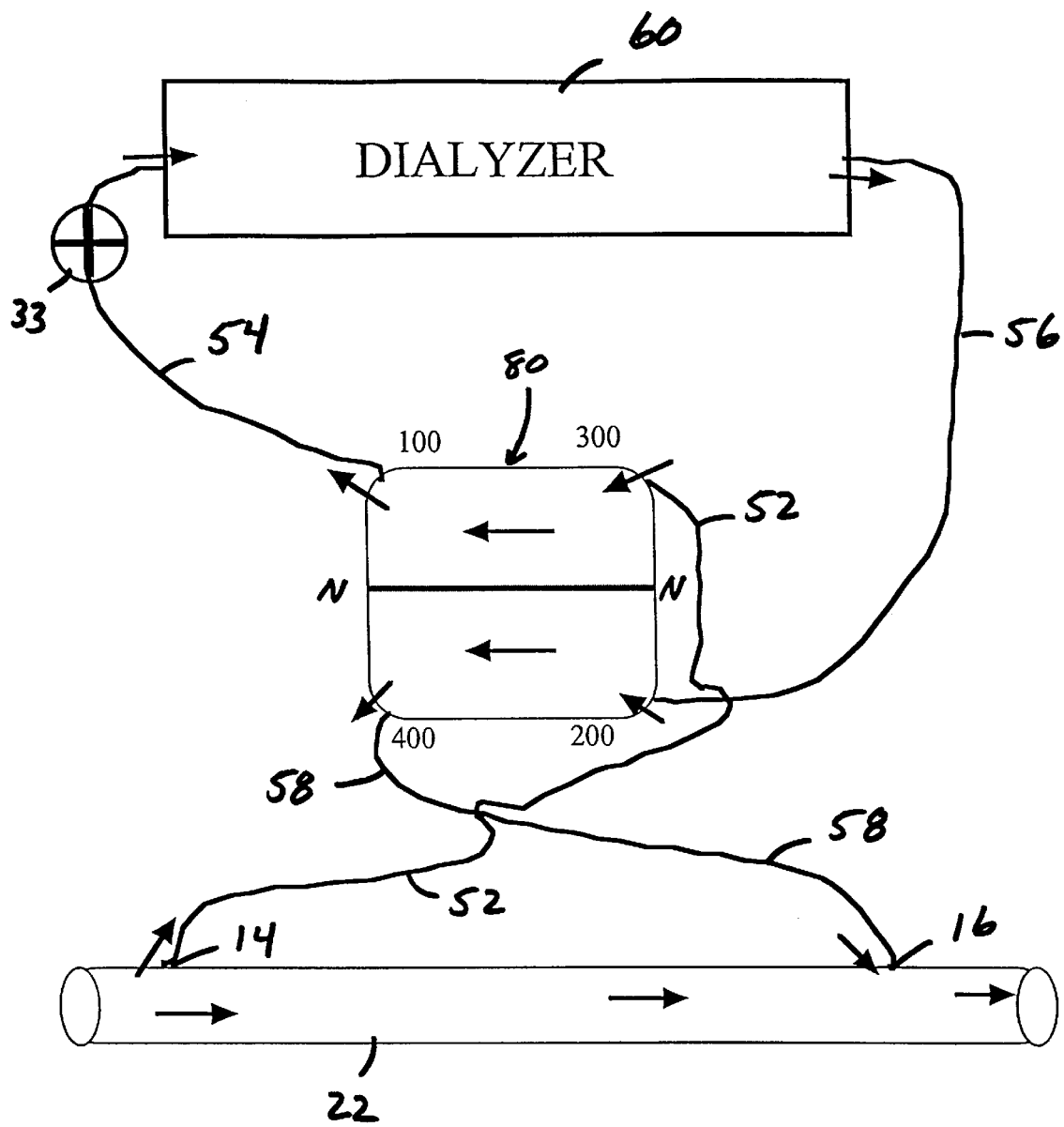
FIG. 7 is schematic view of the diverter in a first extracorporeal circuit in a normal flow clamping.
Figure 9:
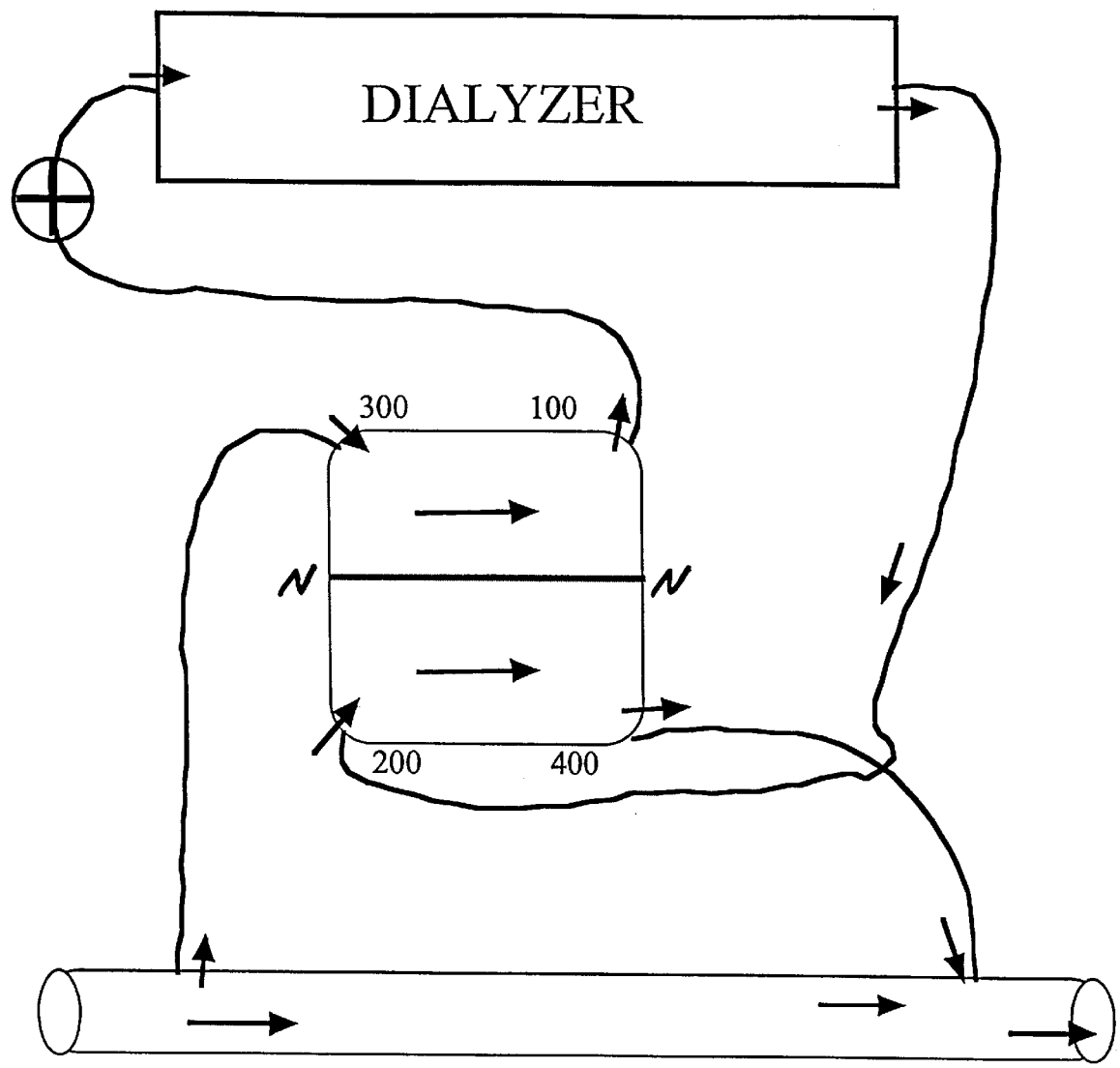
FIG. 9 is schematic view of the diverter in a second extracorporeal circuit in a normal flow clamping.
Figure 11:
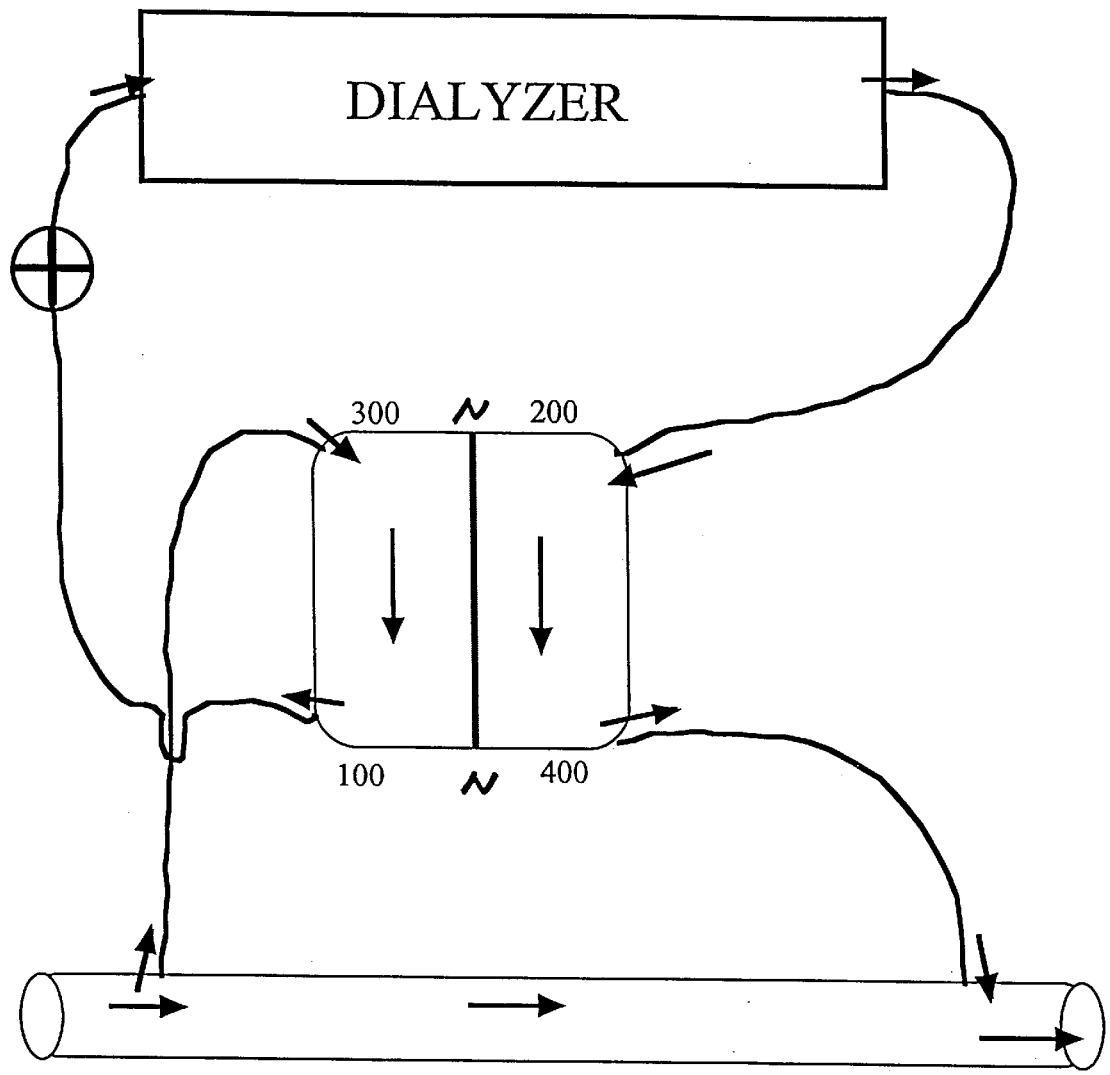
FIG. 11 is schematic view of the diverter in a third extracorporeal circuit in a normal flow clamping.

To establish a normal direction flow through the extracorporeal circuit 30, the common chamber 82 is deformed to contact opposing interior surfaces 83 along line N—N of FIGS. 7, 9 and 11. Deformation of the common chamber 82 can be accomplished through a variety of clamping and pinching devices including but not limited to a hemostat or special device that acts like hemostat. Clamping along line N—N contacts opposing portions of the interior surface 83 and places ports 100 and 300 in fluid communication while ports 200 and 400 are fluidly connected to each other. There is no flow path between ports 100 or 300 to ports 200 or 400. Thus, blood flows from the patient access 22 into the upstream needle 14 and through the upstream line 52 through port 300 and into half of the common chamber 82. Flow to ports 200 or 400 is precluded by the contacting interior opposing surfaces 83 of the common chamber 82. Blood then flows from the half of the common chamber 82 through port 100 to the dialyzer arterial line 54 and into the dialyzer 60. The blood passes from the dialyzer 60 through the dialyzer venous line 56 to port 200 of the common chamber 82. As the blood cannot pass to ports 100 or 300, the blood flows out of the common chamber 82 through port 400 to the downstream line 58. Blood passes through the downstream line 58 to enter the patient access 22 through the downstream needle 16.

Figure 8:
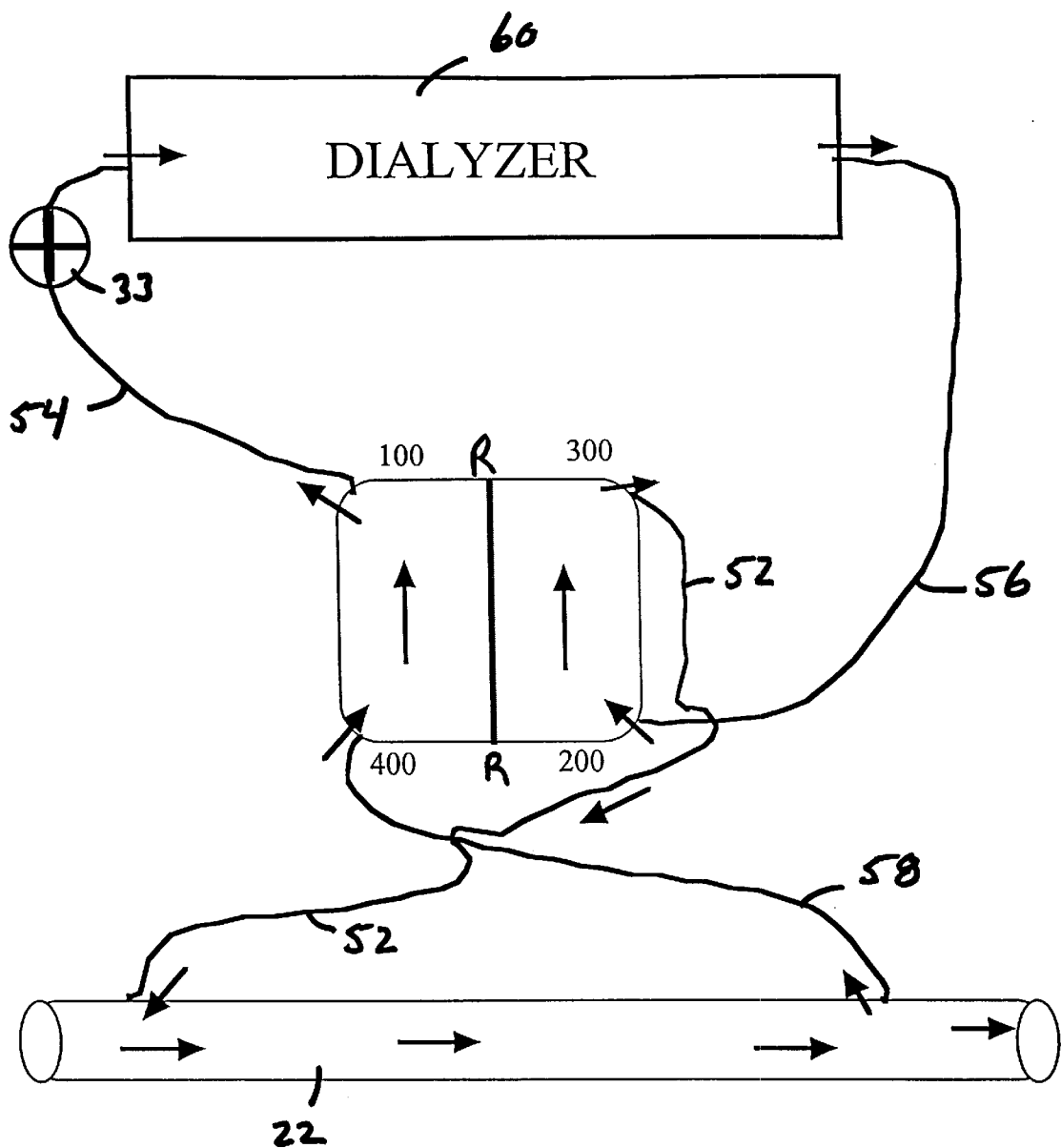
FIG. 8 is schematic view of the diverter in the first extracorporeal circuit in a reverse flow clamping.
Figure 10:
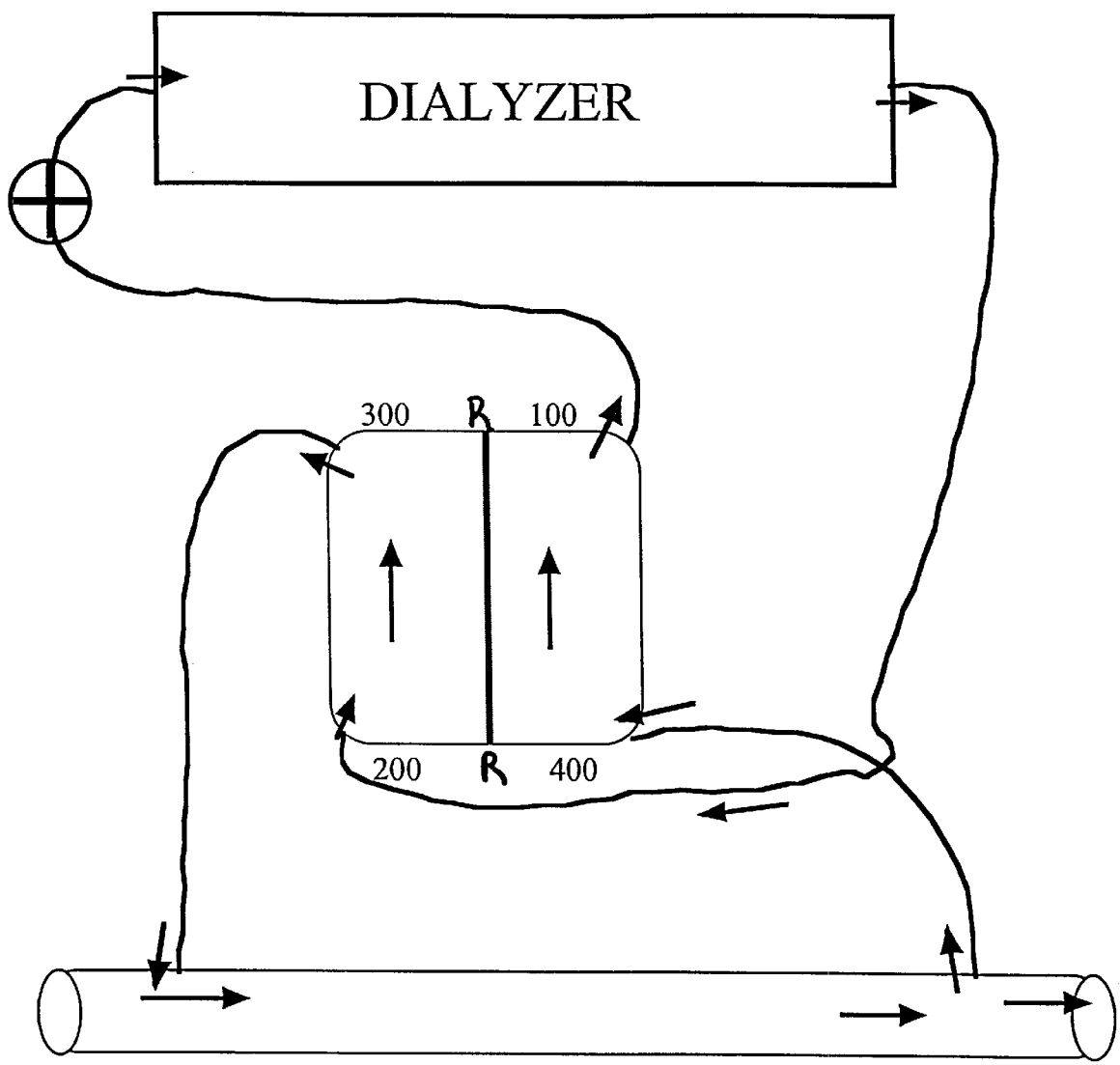
FIG. 10 is schematic view of the diverter in the second extracorporeal circuit in a reverse flow clamping.
Figure 12:
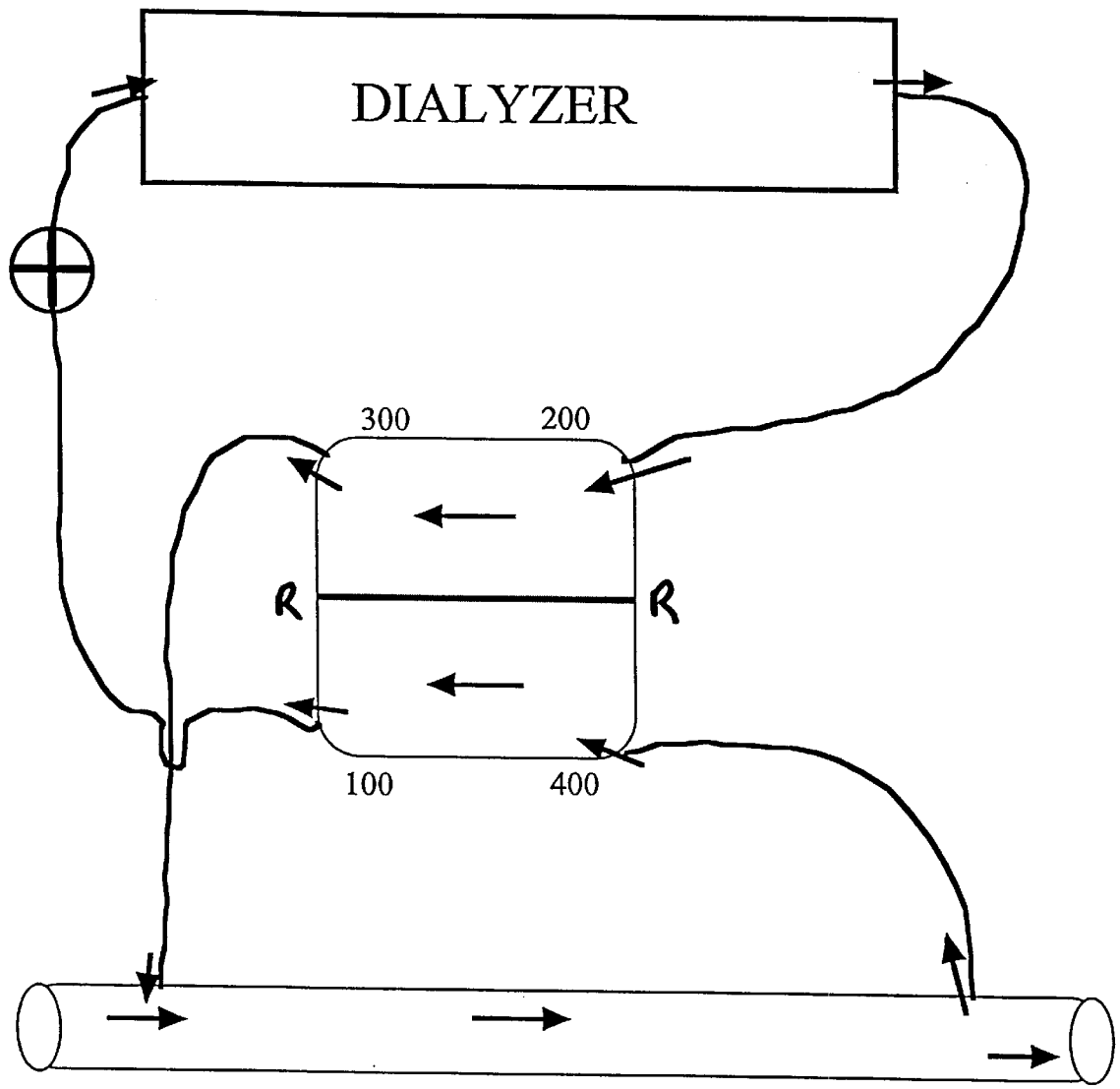
FIG. 12 is schematic view of the diverter in the third extracorporeal circuit in a reverse flow clamping.

The blood flow in the two lines that are connected to the needles will be changed according to the position of the clamping system that divides the common chamber 82 into two parts. Specifically, to reverse the blood flow with respect to the upstream needle 14 and the downstream needle 16, the clamp is removed from along lines N—N to then clamp along lines R—R, as shown in FIGS. 8, 10 and 12. Upon clamping along lines R—R, ports 100 and 400 are in fluid communication and ports 200 and 300 are in a separate fluid communication.

In this clamping configuration, blood is draw from the patient access 22 through the downstream needle 16 to pass through the downstream line 58, through port 400 and into a divided half of the common chamber 82. The blood flows through port 100 and into the dialyzer arterial line 54 to enter the dialyzer 60. The blood exits the dialyzer 60 and passes through the dialyzer venous line 56 to enter a divided half of the common chamber 82 through port 200. The blood passes from the divided half of the common chamber 82 through port 300 into the upstream line 52 to pass through the upstream needle 14 and enter the patient access 22.

Thus, by selectively clamping the common chamber 82 along the clamping lines N—N or R—R, blood may selectively removed from an upstream location in the patient access 22 to be returned at a downstream location in the patient access, or removed from a downstream location in the patient access to be returned to the patient access at an upstream location, respectively.

In an alternative configuration, the common chamber 82 may include the baffle rotatably connected to at least one of the top wall 86 and the bottom wall 88 as shown in FIGS. 13–16. The applications of the flow diverter are wide spread. For example, at a time when vascular access hemodynamics were less well understood, flow within the access had been identified as a parameter associated with vascular access dysfunction, however, the early method of measuring flow was expensive and was not easily performed. With the advent of the indicator-dilution method for measuring access flow, research activities surrounding flow within the access as a predictor of access dysfunction intensified. The resultant explosion of research has resulted in a wealth of data supporting the ultrasound-dilution method as a reliable technique, and has established a strong relationship between low or rapidly declining access flow and the onset of serious stenosis and access dysfunction.

It has been found in this dilution technology, that reversal of blood flow in certain sections of the extracorporeal circuit are advantageous. The ultrasound dilution measurements requires line reversal, a process by which the arterial and venous blood lines are disconnected from their respective needles and cross connected, temporarily, in order to create conditions within the access which make the measurement possible. Despite the non-invasive and innocuous nature of the measurement device and indicator, the reversal of lines proves a stumbling block in the mass distribution and implementation of these valuable measurements. It is the line reversal process that most people regard as the methods' only fallacy, not only for the possibility of contamination of the circuit by microbes or air bubbles, but also because of the additional time required to complete this process. In an effort to solve these problems and extend usage of the ultrasound-dilution technique access flow measurements in strategies aimed at reducing vascular access morbidity, the present invention provides a simple means of reversing the arterial and venous blood lines for vascular access blood flow measurement.

The subject invention avoids disconnecting the blood lines, thus reducing the possibility for contamination of the extracorporeal circuit. The invention also minimizes the chance for thrombus formation within the diverter itself by eliminating areas of stagnant blood flow.

Reversal of blood lines is also useful in dialysis catheters. Frequently, dialysis center personnel will manually reverse the blood lines in order to achieve greater flow to the dialyzer while reducing negative pressure in the arterial line which may cause blood cell damage. Additionally, this strategy may be employed in order to reduce or eliminate recirculation in a catheter. The subject invention offers a rapid means of reversing blood lines to achieve optimal treatment in catheters.

The invention thus provides a means of reversing the direction of flow in the extracorporeal portion 30 of the blood circuit. This reversal can be accomplished easily without disconnecting the lines during treatment and without shutting off and restarting the dialysis machine 60. Flow through the dialysis machine 60 continues uninterrupted during switching. Further, this invention can be fabricated to comprise a low cost sterile disposable unit that, in its preferred embodiment, includes a single deformable resilient component. The present invention also enables the user to choose an inlet/outlet configuration that minimizes the pressure differential, thereby maximizing flow through the dialysis machine.

Minimizing the amount of turbulence associated with blood flow through the device is accomplished by ensuring that channels are aligned, without sharp bends or turns, and sized to be compatible with the inner cross section of the blood lines. The device 80 reduces opportunities for clotting and/or stagnation of blood flow because it contains no sharp turns or changes in diameter in the fluid fittings, thereby promoting laminar flow.

The present invention also promotes safety in use in a number of ways. First, the design configuration is very simple and suitable for mass production as a sterile disposable, thereby minimizing the possibility of infection from using the device. Second, it is not complicated to operate. Third, the invention allows flow to be reversed manually without requiring the application of undue force or mechanical assistance. Fourth, the invention maintains the sterile conditions in the entire blood circuit during the flow reversal operation. The invention does not allow air to enter the blood circuit or blood to be lost during flow reversal.

Although the present invention has been described in terms of particular embodiments, it is not limited to these embodiments. Alternative embodiments, configurations or modifications which will be encompassed by the invention may be made by those skilled in the art, particular in light of the foregoing teachings. Alternative embodiments, configurations, modifications or equivalents may be included in the spirit and scope of the invention, as defined by the appended claims.

What is claimed is:

1. A method of reversing a blood flow between a patient access and a dialyzer, the patient access having an upstream port and a downstream port, the dialyzer having an inlet and an outlet, comprising:

(a) fluidly connecting a first port of a deformable chamber to the upstream port;

(b) fluidly connecting a second port of the deformable chamber to the dialyzer inlet, the second port adjacent the first port;

(c) fluidly connecting a third port of the deformable chamber to the downstream port, the second port being immediately intermediate the first port and the third port;

(d) fluidly connecting a fourth port of the deformable chamber to the dialyzer outlet port, the fourth port being immediately intermediate the first port and the third port; and (e) selectively deforming the chamber along a first clamp line to contact opposing interior surfaces of the chamber, the contacting interior surfaces along the first clamp line precluding fluid flow in the chamber from the first and second ports to the third and fourth ports.

2. The method of claim 1, further comprising selectively deforming the chamber along a second clamp line to contact opposing interior surfaces of the chamber, the contacting interior surfaces along the second clamp line precluding fluid flow in the chamber from the first and fourth ports to the second and third ports.

3. A method of reversing a flow between a dialyzer and a patient access, the dialyzer having a blood inlet and a blood outlet, and the patient access having an upstream port and a downstream port, the method comprising:

(a) selectively deforming a chamber along a first clamp line to selectively contact opposing interior surfaces to form a first fluid barrier within the chamber and preclude fluid flow across the first fluid barrier, the chamber having a first port fluidly connected to the upstream port, a second port immediately adjacent the first port and fluidly connected to the blood inlet, a third port immediately adjacent the second port and fluidly connected to the downstream port and a fourth port immediately adjacent the first port and the third port and fluidly connected to the blood outlet, the first fluid barrier precluding flow from the first and second ports to the third and fourth ports.

4. The method of claim 3, further comprising deforming the chamber along a second clamp line to selectively contact opposing interior surfaces to form a second fluid barrier within the chamber and preclude fluid flow across the second fluid barrier, the second fluid barrier precluding flow from the first and fourth ports to the second and third ports.

5. A method of interconnecting a patient access and a dialyzer, comprising:

(a) connecting an upstream line from the patient access to a first port of a resilient deformable chamber of a flow diverter;

(b) connecting a dialyzer arterial line from an inlet of the dialyzer to a second port of the resilient deformable chamber, the second port immediately adjacent the first port;

(c) connecting a dialyzer venous line from an outlet of the dialyzer to a third port of the resilient deformable chamber, the third port immediately adjacent the first port;

(d) connecting a downstream line from the patient access to a fourth port of the resilient deformable chamber, the fourth port immediately adjacent the second port and the third port; and (e) deforming the resilient deformable chamber to contact opposing interior surfaces of the chamber and preclude flow from the first and second ports to the third and fourth ports.

6. The method of claim 5, further comprising deforming the resilient deformable chamber to contact opposing interior surfaces of the chamber and preclude flow from the first and third ports to the second and fourth ports.

7. A hemodialysis circuit for fluidly connecting a dialyzer to a patient access for withdrawing blood from the patient access, passing the blood through the dialyzer and introducing the blood into the patient access, comprising:

(a) a resilient deformable chamber having a first port, a second port, a third port and a fourth port, the chamber having a pair of opposing interior surfaces, the interior surfaces having a contour selected to continuously contact the interior surfaces along a first clamping line and a second clamping line to form a full flow barrier along the respective clamping line, the first clamping line precluding fluid flow from the first and fourth ports to the second and third ports and the second clamping line precluding fluid flow from the first and third ports to the second and fourth ports;

(b) a dialyzer arterial line extending from the first port to the a dialyzer inlet;

(c) a dialyzer venous line extending from a dialyzer outlet to the second port;

(d) an upstream line extending from the patient access to the third port; and (e) a downstream line extending from the patient access to the fourth port.

8. The hemodialysis circuit of claim 7, wherein the first, the second, the third and the fourth ports are equally spaced about a periphery of the chamber.

9. The hemodialysis circuit of claim 7, wherein the contour includes a smooth surface.

10. The hemodialysis circuit of claim 7, wherein the contour includes opposing contours sufficient to maintain an engaged relation independent of a deforming force.

* * * * *